United States Patent [19]

Michalchik

[11] Patent Number: 4,776,515

[45] Date of Patent: Oct. 11, 1988

[54] ELECTRODYNAMIC AEROSOL GENERATOR

[75] Inventor: Michael Michalchik, Newport Beach, Calif.

[73] Assignee: Froughieh Michalchik, Newport Beach, Calif.

[21] Appl. No.: 894,360

[22] Filed: Aug. 8, 1986

[51] Int. Cl.$^4$ .............................................. B05B 5/02
[52] U.S. Cl. ........................................ 239/3; 239/706; 417/51
[58] Field of Search ............... 422/4, 123; 239/3, 690, 239/707, 34, 706; 417/48, 50, 51; 427/27, 30; 55/107; 361/228

[56] References Cited

U.S. PATENT DOCUMENTS

| | | | |
|---|---|---|---|
| 705,697 | 7/1902 | Morton | 239/690 X |
| 3,152,762 | 10/1964 | Englehart | 422/4 X |
| 3,247,374 | 4/1966 | Wintermote | 422/4 X |
| 3,296,491 | 1/1967 | Brown | 239/3 X |
| 3,384,446 | 5/1968 | Ziems et al. | 422/123 X |
| 4,356,528 | 10/1982 | Coffee | 239/690 X |
| 4,419,326 | 12/1983 | Santini | 422/4 |
| 4,477,414 | 10/1984 | Muramoto et al. | 422/123 X |

FOREIGN PATENT DOCUMENTS 312340 12/1956 Switzerland ......................... 427/30

Primary Examiner—Andres Kashnikow
Assistant Examiner—Kevin P. Weldon
Attorney, Agent, or Firm—Leonard Tachner

[57] ABSTRACT

An apparatus for generating a mist of negatively charged liquid particles comprises a liquid container, a capillary tube in fluid communication with the container, an electrode at least partially within the passage of the capillary tube and a DC power supply providing a negative potential of at least 5,000 Volts to said electrode. The liquid may be water or other fluids as long as the resistivity of the liquid is in the range of $1.6 \times 10^3$ to $4.0 \times 10^5$ Ohms-centimeters. A preferred embodiment utilizes a negative potential of between 5,000 and 8,000 Volts DC and a liquid having a resistivity in the range of $2 \times 10^4$ to $15 \times 10^4$ Ohms-centimeters.

2 Claims, 1 Drawing Sheet

ELECTRODYNAMIC AEROSOL GENERATOR

BACKGROUND OF THE INVENTION

1. Field of the Invention

This invention relates generally to a method and apparatus for electrically dispersing ionized fluids as an aerosol for improving air quality and more specifically, to a method and apparatus for generating a negative ion aerosol comprising ozone-free negative ions.

2. Prior Art

U.S. Pat. No. 3,085,749 to Schweitzer et al is directed to an electrostatic spray head and includes a head coupled to a shaft through a chuck. High electrical potential for the head is supplied from a source of high voltage through a slip-ring. A fluid such as paint is supplied to the head from a nozzle. The object is mounted in front of the head and is coupled to ground. This reference does not take place the electrode within the fluid.

U.S. Pat. No. 3,296,491 to Brown is directed to a system for producing ions and electrically charged aerosols. The structure includes an elongated electrode which is coupled to the edge of a vane electrode by insulators. The electrodes are maintained at different electrical potentials by the power supply.

U.S. Pat. No. 2,655,107 to Godbold is directed to an electromagnetic fluid pump. In order to produce a flow force on the liquid in a duct, a pair of contacts are provided on the duct. The contacts may penetrate the duct if the duct is of a dielectric material.

U.S. Pat. No. 4,431,137 to Prewett et al is directed to systems for spraying liquid metals. An electric field to disrupt the film of liquid metal forming over an emitting point is applied to the source by an extraction electrode and a terminal.

U.S. Pat. No. 4,264,641 to Mahoney et al is directed to an apparatus for electrohydrodynamic spraying of molten metal (conductive) materials to produce thin film coatings.

The prior art reveals that it is known that a liquid can be dispersed with electrification and that one such dispersal mechanism can consist of a capillary filled with distilled water which forms a fountain with positively charged electrification. The prior art patents show electrodes in close proximity to achieve high electric fields. However, the prior art fails to show the manner required to create a negative ion generator using water as a medium. This is because two essential ingredients of the present invention are missing. More specifically, there is no showing that water forms a dispersion from a negative electrode in the range of voltages suitable for safe ion generation. Secondly, there is no showing that placing a negative electrode in contact with the liquid going into a capillary causes a dispersion to form from the tip of the capillary with any water composition in the voltage and current range under 15,000 Volts and less than one milliAmp. For example, in the Brown patent, a complex apparatus is described having veins and grids in structures designed to form ions with electrohydrodynamic and electrokinetic forces. The liquids disclosed for use in the Brown patent are ionized by high voltage ultraviolet and nuclear sources and then propelled with shaped electrical fields into the atmosphere to produce the desired aerosol. This patent indicates that the operating range is between 10 and 70 kiloVolts using a fine tungsten or stainless steel wire as an electrode. No characteristics of the liquid are specified and the output charge in the atmosphere is not described. More specifically, for the level of voltages specified the generation of ozone may reach intolerable levels particularly at low humidity.

In an early patent, namely, U.S. Pat. No. 705,691 to Morton dated 1902, an electrically polarized atmosphere is produced by passing an electric current of high tension through the atmosphere. Two electrodes are shown by Morton and little description is made of the liquid properties except as mixtures for separation. Morton is clearly interested in separating components of a liquid mixture and not in optimally placing charges into the air. The only dispersive effect apart from separation is the apparent improvement in the evaporation of the more volatile components of the liquid. Furthermore, Morton specifically refers to the production of ozone which he relies upon to ozonize the material in the process of forming the separating. All cited examples of the prior art and specifically U.S. Pat. No. 705,691 assume that electrode contact with the liquid is all that is required. However, the applicant has discovered that merely contacting the liquid in the spraying of water does not produce a fountain, in fact, except for the invention disclosed herein, water cannot be sprayed without a system that is predominantly mechanical. All prior low voltage systems not used for precipitation of particles and other systems of high voltage designed for use outdoors use electrostatic fields to aid in the placement of droplets or in electrohydrodynamic propulsion in outer space.

SUMMARY OF THE INVENTION

The theory of the present invention is based upon the accepted concept of hydrogen bonding in polar liquids. It is well known that the associative property of water with its high boiling point and high heat capacity is due to the affinity of the hydrogen atom in one molecule for the oxygen atom in an adjacent molecule. Indeed water has been postulated with a variable degree of rotational and vibrational freedom depending upon temperature. The degree of association of the atoms in water appears to cause a spectral line which forms in addition to the hydrogen bonding spectra. These weak lines change over the range from freezing to boiling of the water in the liquid state and are only slightly affected by pressure up to the critical point. Molecular orbital studies show that a great deal of shielding is possible around clusters of associated molecules. These shielded clusters, in effect, suggest energy quanta much as the phenomenon of energy transfer by phonons in crystal lattices.

Judging from the large charge acceptance (e/m ratio) of the water particles as generated in the inventive process and device, it could be postulated that water can be preferentially dispersed under conditions of "super" charge acceptance due to quantized energy which might be termed "quantons" in a highly polar liquid. Effective dispersion occurs when the dielectric field and hydrodynamic flow establish a condition of resonance of forming quantons in a liquid and yielding uniquely electron rich "cages" in the associated liquid structure. The resonance of the quanton "cages" is the medium for accepting charge on a multimolecular level and subsequent evaporation after dispersion of liquid droplets induces an extraordinary penetrating diffusion of charges from electrons partially shielded in trapping structure with suitably composed droplets. The release of charge substantially above the possible level of homogeneous molecular water is not unlike the activation states explaining lasers and masers. Instead of achieving pure electromagnetic radiation however, a quantized super distribution of charge occurs at a phenomenally rapid rate in space under conditions of decreasing electric field intensity, such as in emission from a laser window. Charge is transferred more controllably from shielded molecular clusters and electron cages to smaller polar molecules in a field weaker than the point of origin and diffuse into air and surfaces with which contact is made.

As a result, the present invention is capable of generating an aerosol of negative ions over a large radius and apparently independent of air diffusion and movement in relatively weak fields. Pure distilled water can form a fountain out of positive potential but cannot do so from a comparative negative potential. The reason for this may be determined by examining the charge acceptance of molecular water (the hydronium ion resulting from water ionization is positive). It remains that from conventional theory, one cannot postulate that water will effectively ionize negatively due to the small radius of the hydroxyl ion maintaining charge equilibrium in bulk water. The present invention modifies the water by in effect "doping it" to form clusters with an electron cage effect.

The inventor has hypothesized that water exists in an associated form with discrete quantons of shielded molecules and resonant electrical negative charge. This hypothesis is an explanation of an astonishing level of negative ions measured using the present invention and the extraordinary rapidity of charge diffusion over distances of meters within a few seconds. The quanton concept is supported by the evidence that a comparable amount of liquid sprayed at the identical voltage from the positive electrode produces a relatively weak positive charge. Thus, the present invention relies upon the fact that the liquid characteristics are critical to the quantity of charge developed in the atmosphere. Most importantly, the proper dispersion of water according to the present invention results in the suppression of ozone formation.

The invention has resulted from multiple discoveries related to capillary tube configuration, liquid composition and an overall system for generating ion effects. The invention is based upon the finding that water can carry a negative charge and even form explosive droplets when the resistivity is in the range of $1.6 \times 10^3$ to $4 \times 10^5$ Ohms-centimeters and between 3.5 and 14 kiloVolts is applied. It has been found that one embodiment of the present invention can produce continuous atomization by using a fine tipped capillary of between 0.5 and 4.0 millimeters drawn to a fine point with a sharp radius of curvature and further by inserting a fine wire electrode wire into the opening at the bottom of the capillary and applying between 5 and 8 kiloVolts of negative polarity using water in the resistivity range of 2 to $15 \times 10^4$ Ohms-centimeters. Furthermore, the present invention relies upon connecting a power supply with positive pole to ground and negative pole to the electrode in the capillary which creates an extremely powerful and efficient generator of negatively charged particles (ions). Essentially, no ozone is generated and the charge level exceeds by two orders of magnitude the charge level attainable with point sources and wire electrodes discharging into the air.

The resulting apparatus is an unexpected means for the regulation of minute quantities of substances for continuous aerosol release which cannot be obtained by air operated negative ion generators.

The present invention is not limited to the electrodynamic atomization of water. It may also be used for the atomization of alcohol, perfume, ammonia and many other constituents which are sprayed from the capillary orifice and instantly dispersed throughout an open area without dependence on air currents. Thus, the walls of a room act as opposing electrodes and an area of precisely metered quantities of any dispersible medications and other compounds can be administered for inhalation. Moreover, it has been found that smoke and sulfurous odors are dispersed and neutralized in the presence of the aerosol from the electrodynamic discharge of the present invention.

Perhaps the most interesting application of the present invention is its use for generating an aerosol on a continuous basis in areas of public passage and gatherings to suppress the communication of infectious airborne diseases. Such advantageous applications would find particular attraction in hospitals, restaurants, physician's offices and in other areas where large groups may gather in relatively small places or where it is highly likely that one or more people contained within a defined space has a communicable disease.

OBJECTS OF THE INVENTION

It is therefore a principal object of the present invention to provide a liquid-based negative ion generator for producing charged liquid aerosols.

It is an additional object of the present invention to provide an electrodynamic fine particle generator for creating a charged liquid aerosol while generating little or no ozone.

It is still an additional object of the present invention to provide a negative ion aerosol device which utilizes a fine tipped capillary and fine negative electrode inserted into the opening of the capillary to impart a negative charge to specially prepared liquid to form microatomized droplets.

It is still an additional object of the present invention to provide an electrodynamic fine particle generator capable of generating liquid based negative ions without requiring more than about 9,000 Volts for projecting charged particles over large distances without relying on air movement.

It is still an additional object of the present invention to provide an electrodynamic fine particle negative ion generator adapted to work with such liquids as water, alcohol, perfume, ammonia as well as liquid medications and surfactants to instantly disperse into an open area an aerosol containing such constituent components and for neutralizing or removing from such open area unpleasant smoke and other odors that may be contained therein.

It is still an additional object of the present invention to provide an electrodynamic fine particle negative ion generator capable of improving the quality of air conditioning by controlling the environmental content and flow of negative ions.

BRIEF DESCRIPTION OF THE DRAWINGS

The aforementioned objects and advantages of the present invention as well as additional objects and advantages thereof will be more fully understood hereinafter as a result of a detailed description when taken in conjunction with the accompanying drawings in which.

DETAILED DESCRIPTION OF THE INVENTION

Figure 1:
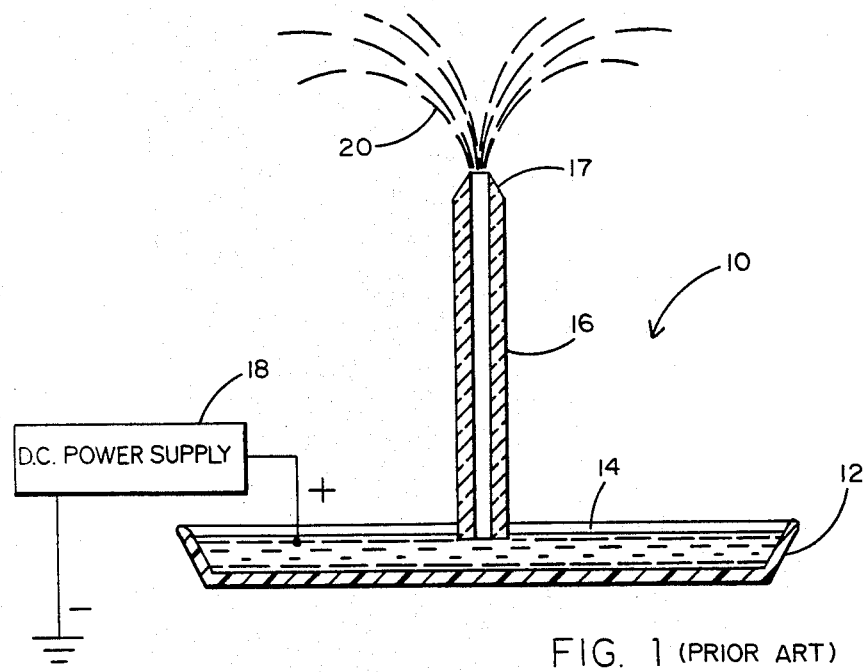
FIG. 1 is a representation of a prior art electrically driven fountain.

The most relevant prior art known to the application is shown in FIG. 1 which illustrates a prior art electrodynamic fountain 10 comprising an insulating dish 12 containing a quantity of distilled water 14 and having a capillary 16 extending vertically therefrom and terminating in a capillary tip 17 which is drawn to a fine point with a sharp radius of curvature. A DC power supply 18 is provided, the positive electrode or pole of which is in contact with the distilled water 14 and a negative electrode or pole of which is grounded. DC power supply 18 must generate a voltage of at least 10,000 Volts. Upon application of the high voltage from DC power supply 18 to the distilled water 14, an electrodynamic pumping effect occurs in which the highly purified water is pumped up the capillary and the water is ejected from the tip. The effect is to form an electrically driven fountain. Of interest is the fact that the electrical resistance of distilled water is a minimum of $18 \times 10^6$ Ohms-centimeters.

Figure 2:
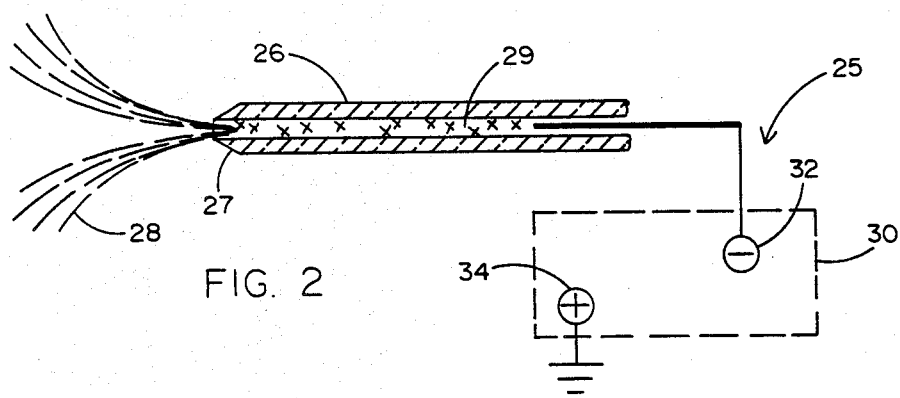
FIG. 2 is a schematic illustration of the present invention.

The present invention results from the surprising finding that water can carry a negative charge and be caused to form explosive droplets when its resistivity is in the range of $1.6 \times 10^3$ to $4 \times 10^5$ Ohms-centimeters and between 3,500 and 14,000 Volts is applied. In addition it has been found surprisingly that one can generate a continuous atomization of the water by using a fine tipped capillary of for example, 4.0 millimeters drawn to a fine point with a sharp radius of curvature having an exit aperture of about 0.5 millimeter, inserting a fine electrode wire into the opening at the base of the capillary, by applying between 5,000 and 8,000 Volts negative polarity and using water in the resistivity range of 2 to $15 \times 10^4$ Ohms-centimeters. This finding is illustrated in FIG. 2 wherein it is shown that an electrodynamic aerosol device 25 comprises an elongated capillary 26 having a drawn tip 27 for generating a fine mist 28 comprising negatively ionized particles of water supplied by a fluid column 29 within the capillary 26. Unlike the prior art of FIG. 1, the liquid electrodynamic device of the present invention utilizes a DC power supply 30 in which the negative electrode or pole 32 is connected for application of negative voltage to the water column 29 while the positive electrode of pole 34 is grounded. It has been found that by connecting the power supply with positive electrode to ground and negative electrode connected to the capillary water column, an extremely powerful and efficient generator of negatively charged particles or ions is created. Essentially no ozone is generated and the charge level exceeds by two orders of magnitude the charge level attainable with present day commercially available negative ion generators which use point sources and wire electrodes discharging into the air.

Figure 3:
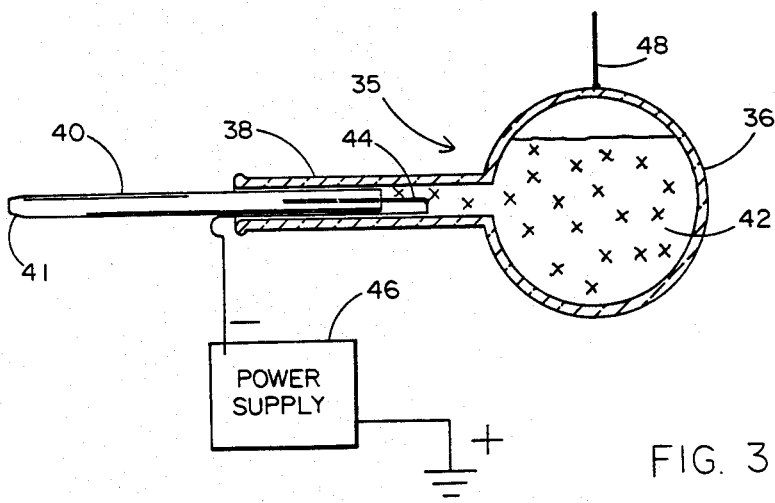
FIG. 3 illustrates an actual embodiment of the present invention that has been reduced to practice.

An actual reduction to practice of the present invention is illustrated in FIG. 3. More specifically, FIG. 3 illustrates a negative ion aerosol generator 35 comprising a glass flask 36 provided with a neck 38 having a capillary tube 40 partially inserted therein. Capillary 40 is provided with a drawn tip 41. The flask 36 contains a selected quantity of a conductive liquid 42 which also fills the capillary 40. The base of capillary 40, that is, the portion thereof that is contained within the neck 38 of flask 36, is provided with a fine wire electrode 44 extending partially therethrough, the electrode 44 being connected to a DC power supply 46 and more specifically, to the negative electrode thereof. The positive electrode of power supply 46 is grounded. Power supply 46 is preferably capable of providing between 5 and 10 kiloVolts DC, variable over that range in order to provide control of the volume of mist generated by the present invention. Power supply 46 can be a pulsed DC source as well as being a steady state DC source. The flask 36 may optionally be provided with a vent tube 48 to provide a means for permitting vapor and liquid equilibrium to overcome the negative pressure formed as liquid is discharged from container flask 36.

A critical and necessary element of the present invention is the electrical characteristic of the liquid contained within the flask 36. As previously indicated, this liquid should have a resistivity in the range of $1.6 \times 10^3$ to $4 \times 10^5$ Ohms-centimeters. By the use of soluble alcohols and polyhydric compounds of high water compatibility of up to 25% by weight of the liquid composition, but preferably under 5% by weight, the optimal range in which a composition can be dispensed will vary in resistivity by a factor of 2 to 10 depending upon the overall dielectric characteristics of the liquid. The best dispensing and aerosol propagation characteristics for a given liquid remain in specific conductivity range and will change very little with nozzle or capillary tip design. The output in milliliters of liquid per hour can be substantially changed by varying the DC output voltage.

Colloidal suspensions and dispersions of small particles with low ionization constants such as zinc oxide can be included in the liquid to be sprayed for inhalation therapy and the metering of medication for prolonged low level dosages. The invention is an unexpectedly excellent means for the regulation of minute quantities of substances for continuous aerosol release which cannot be achieved by air operated negative ion generators. The present invention can be used to atomize other liquids such as medicinals, surfactants, anti-infectives, alcohols, perfumes, ammonia and other constituents for dispersing same around an open space substantially without dependence on air currents. The walls of the room in which the present invention is utilized act as opposing electrodes and an area of precisely metered dimensions can be substantially filled with dispersible medications or other compounds for inhalation purposes.

Interestingly, it has been found that the insertion of the electrode into the capillary of the present invention is also a requirement for its operation. No mist or other form of fountain-like output can be formed from the flask by merely contacting the liquid with the power supply electrode. Withdrawal of the electrode from the capillary even after spraying has been initiated and while fluid contact is maintained, still causes a cessation of spraying. Only with water and similar liquids in the particular electrical condition defined herein and with the capillary and electrode contact defined herein, can the effect of the present invention be produced. The capillary column must be continuous and unbroken with an air or gas bubble to operate with the emission of atomizing spray which is directed somewhat in the direction of the nozzle. Failure to maintain a continuous column of fluid may result in an arc-type ozone forming phenomenon, which is undesirable. The emission at about 3 to 5 centimeters from the nozzle or capillary tip has been measured at up to 40 micro-Amperes which corresponds to an electron flow of $3 \times 10^{14}$ per second for an electrode potential in the range of 6,000 to 10,000 Volts. The voltage measurable at about 3 meters from the nozzle or tip at an individual holding a multimeter probe, was approximately $-100$ millivolts. No measurable level of ozone was detected.

It will now be understood that what has been disclosed herein comprises an entirely unique means for generating aerosols of negative ion particles using liquids having specified electrical characteristics to which a negative voltage is applied from a power supply for generating a fine mist spray from the drawn tip of a capillary tube into which the negative electrode or pole of the power supply is inserted. A substantial negative charge is imparted to the liquid particles causing them to rapidly disperse within a defined space to the outlying walls thereby clearing the air of dust, bacteria, and disease borne particles which might otherwise detrimentally affect of the occupants. In addition, the present invention is particularly suitable for removing odors such as those resulting from smoke and the like. The invention may also be used for enabling the continuing inhalation of medication by merely adding the medication as a constituent part of the liquid to which the negative voltage is applied. A particular embodiment that has been reduced to practice is disclosed herein and comprises a flask filled with specially treated water to provide the liquid electrical characteristics needed to generate the aerosol spray in reaction to the application of between 5,000 and 10,000 Volts negative potential to the liquid which is within a capillary tube preferably of selected dimensions and which is provided with an electrode connected to the negative pole of the power supply.

Those having skill in the art to which the present invention pertains will now, as a result of the applicant's teaching herein, perceive various modifications and additions which may be made to the invention. However, all such modifications and additions are deemed to be within the scope of the invention which is to be limited only by the claims appended hereto.

I claim:

1. An apparatus for generating a mist of ozone-free negatively ionized liquid particles, the apparatus comprising:
    a container for holding a selected quantity of liquid;
    a capillary tube having one end in fluid communication with said liquid in said container;
    a power supply capable of generating about 5,000 to 14,000 Volts DC, said supply having a negative pole and a positive pole; and
    an electrode extending into said capillary tube for contact with said liquid;
    said negative pole being connected to said electrode and said positive pole being grounded;
    wherein said liquid has a resistivity in the range of $1.6 \times 10^3$ to $4 \times 10^5$ Ohms-centimeters and comprises water containing less than 25% by weight soluble alcohol and polyhydric compounds.

2. A method for generating an aerosol of ozone-free negatively charged liquid particles, the method comprising the steps of:
    (a) providing a liquid having a resistivity in the range of $1.6 \times 10^3$ to $4 \times 10^5$ Ohms-centimeters and comprising water containing less than 25% by weight soluble alcohol and polyhydric compounds;
    (b) passing said liquid into the passage of a capillary tube of selected dimensions;
    (c) applying a negative voltage of selected magnitude to the liquid in said capillary tube whereby to cause positive ejection, micro-atomization and dispersal of said liquid from said capillary tube while generating substantially no ozone; and
    (b) placing said capillary tube at a preselected distance from any oppositely polarized electrode which would otherwise deflect or absorb the negatively charged particles before dispersal thereof.

* * * * *